(12) United States Patent
Corcoran et al.

(10) Patent No.: US 7,927,351 B2
(45) Date of Patent: *Apr. 19, 2011

(54) OCCLUSION DEVICE WITH FLEXIBLE WIRE CONNECTOR

(75) Inventors: Michael P. Corcoran, Woodbury, MN (US); Joseph A. Marino, Apple Valley, MN (US)

(73) Assignee: Cardia, Inc., Eagan, MN (US)

( * ) Notice: Subject to any disclaimer, the term of this patent is extended or adjusted under 35 U.S.C. 154(b) by 1339 days.

This patent is subject to a terminal disclaimer.

(21) Appl. No.: 11/455,426

(22) Filed: Jun. 19, 2006

(65) Prior Publication Data

US 2007/0293890 A1    Dec. 20, 2007

(51) Int. Cl.
*A61B 17/08*    (2006.01)
(52) U.S. Cl. ......... 606/216; 606/157; 606/213; 606/215
(58) Field of Classification Search ............... 606/213, 606/215, 216, 94, 157; 600/37; 604/96.01, 604/101.2
See application file for complete search history.

(56) References Cited

U.S. PATENT DOCUMENTS

| | | |
|---|---|---|
| 3,874,388 A | 4/1975 | King et al. |
| 4,007,743 A | 2/1977 | Blake |
| 4,284,166 A | 8/1981 | Gale |
| 4,917,089 A | 4/1990 | Sideris |
| 5,092,424 A | 3/1992 | Schreiber et al. |
| 5,108,420 A | 4/1992 | Marks |
| 5,171,259 A | 12/1992 | Inoue |
| 5,284,488 A | 2/1994 | Sideris |
| 5,334,137 A | 8/1994 | Freeman |
| 5,334,217 A | 8/1994 | Das |
| 5,382,260 A | 1/1995 | Dormandy, Jr. et al. |
| 5,397,331 A | 3/1995 | Himpens et al. |
| 5,425,744 A | 6/1995 | Fagan et al. |
| 5,433,727 A | 7/1995 | Sideris |
| 5,451,235 A | 9/1995 | Lock et al. |
| 5,634,936 A | 6/1997 | Linden et al. |
| 5,702,421 A | 12/1997 | Schneidt |
| 5,709,707 A | 1/1998 | Lock et al. |
| 5,725,552 A | 3/1998 | Kotula et al. |
| 5,741,297 A | 4/1998 | Simon |
| 5,904,703 A | 5/1999 | Gilson |
| 5,944,738 A * | 8/1999 | Amplatz et al. ............. 606/213 |
| 6,024,756 A | 2/2000 | Huebsch et al. |
| 6,174,322 B1 * | 1/2001 | Schneidt ........................ 606/213 |
| 6,206,907 B1 | 3/2001 | Marino et al. |
| 6,389,146 B1 | 5/2002 | Croft, III |
| 6,551,344 B2 | 4/2003 | Thill |
| 6,634,455 B1 | 10/2003 | Yang |
| 2004/0044361 A1* | 3/2004 | Frazier et al. ................. 606/200 |
| 2007/0293889 A1* | 12/2007 | Corcoran et al. ............. 606/213 |
| 2007/0293891 A1* | 12/2007 | Corcoran et al. ............. 606/213 |
| 2008/0065148 A1* | 3/2008 | Corcoran et al. ............. 606/213 |

FOREIGN PATENT DOCUMENTS

| | | |
|---|---|---|
| DE | 42 22 291 C1 | 1/1994 |
| EP | 0 362 113 | 4/1993 |
| EP | 0 541 063 | 9/1998 |
| GB | 2 269 321 A | 9/1994 |

* cited by examiner

*Primary Examiner* — (Jackie) Tan-Uyen T Ho
*Assistant Examiner* — Melissa Ryckman
(74) *Attorney, Agent, or Firm* — Kinney & Lange, P.A.

(57) ABSTRACT

An occlusion device includes a flexible section formed by a wire connector. The flexible wire connector gives the occlusion device improved torque and flexure characteristics, which allows the device to better conform to the contours of the heart.

15 Claims, 9 Drawing Sheets

OCCLUSION DEVICE WITH FLEXIBLE WIRE CONNECTOR

BACKGROUND OF THE INVENTION

This invention relates to an occlusion device for repairing cardiovascular defects. More specifically, this invention relates to an occlusion device which has a center assembly including a flexible wire connector that provides improved torque and flexure characteristics and allows the device to better conform to the contours of the heart.

Normally, permanently repairing certain cardiac defects in adults and children requires open heart surgery, a risky, expensive, and painful procedure. To avoid the risks and discomfort associated with open heart surgery, occlusion devices have been developed that are small, implantable devices capable of being delivered to the heart through a catheter. Rather than surgery, a catheter inserted into a major blood vessel allows an occlusion device to be deployed by moving the device through the catheter. This procedure is performed in a cardiac cathlab and avoids the risks and pain associated with open heart surgery. These occlusion devices can repair a wide range of cardiac defects, including patent foramen ovale, patent ductus arteriosus, atrial septal defects, ventricular septal defects, and may occlude other cardiac and non-cardiac apertures. There are currently several types of occlusion devices capable of being inserted via a catheter. The occlusion devices must have sufficient flexibility to accomplish the sharp and numerous turns in the body's vasculature.

Another challenge in deploying an occlusion device in the heart is the variations of the contours of the aperture the occlusion device is meant to close. In particular, when occluding septal defects, the uneven topography in the vascular and septal walls of the human heart makes it difficult to design a device that can adapt to such variations. The challenge in designing an occluder which conforms to the uneven topography is compounded by the fact that the contours of each defect in each individual patient are unique. Poor conformation to the defect results in poor seating of the occlusion device across the aperture, which decreases the ability of the device to successfully occlude the aperture.

Lack of conformation to the walls of the heart can place significant amounts of stress on the occlusion device and decrease fatigue life. Once deployed, different parts of the occluder may experience more or less stress as a result of the uneven topography. At some point, stressed parts of the occluder may break. Broken parts increase the likelihood of damage to the surrounding tissue and lead to patient anxiety.

Another obstacle which may be encountered is the difficulty in readily distinguishing the individual occluder elements in order to determine their position in relation to each other and allow for repositioning, while still maintaining the flexibility needed for better conformation.

Thus, there is a need in the art for an occlusion device that will occlude cardiac defects and will match the contours of the heart thereby increasing the life of the device and its sealing ability while reducing damage to the surrounding tissue. There is also a need for an occlusion device that prevents rotation of the individual occluder elements around the center post, while still maintaining the needed flexibility to properly position the device and successfully match the contours of the heart.

BRIEF SUMMARY OF THE INVENTION

The present invention is an occlusion device having a center assembly that includes a flexible wire connector. The occlusion device has a first occluding body and a second occluding body connected by the center assembly. The center assembly comprises a proximal hub, which is attached to the first occluding body, a distal hub, which is attached to the second occluding body, and a flexible wire connector extending between the proximal hub and the distal hub. The flexible wire connector increases the ability of the occlusion device to more accurately conform to the defect, while still allowing the device to be moved and deployed using a catheter.

DETAILED DESCRIPTION

Figure 1A:
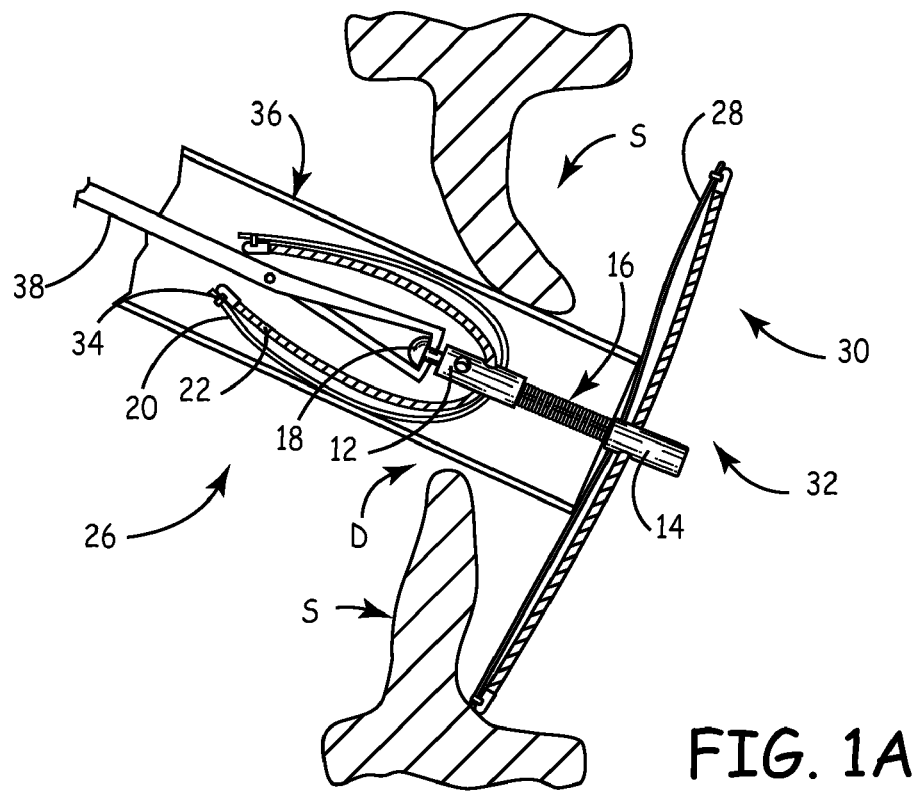
FIG. 1A-1B are diagrams of an occlusion device with a center assembly that includes a flexible wire connector being inserted into a defect.
Figure 1B:
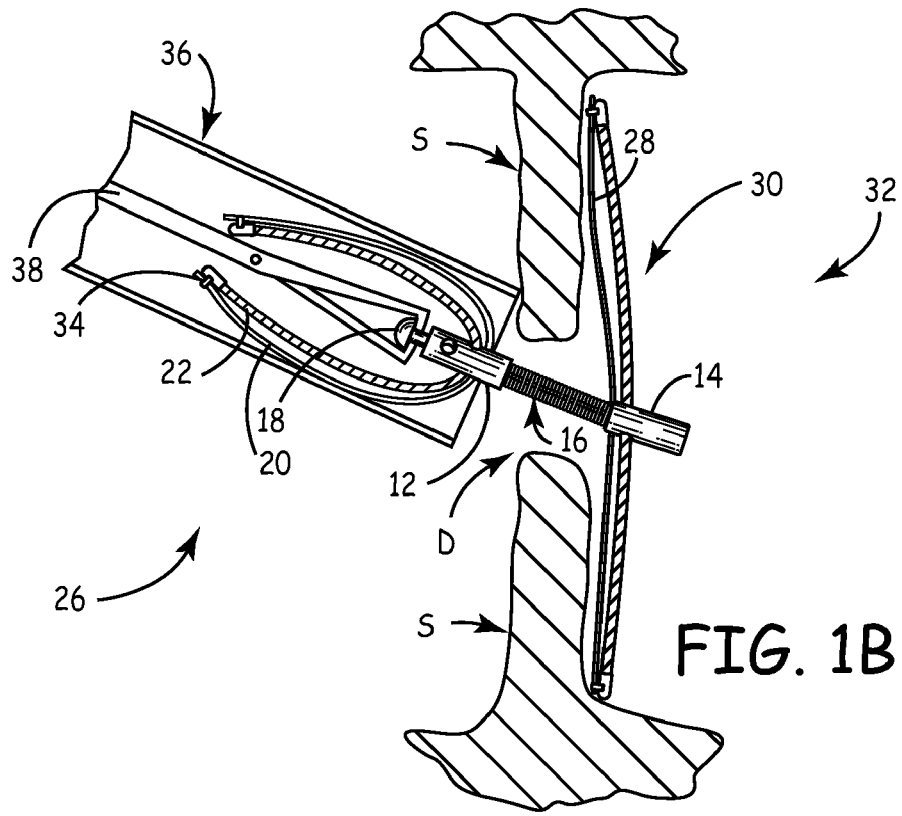

FIG. 1A-1B illustrate how occlusion device 10 having flexible wire connector 16 is deployed. Occlusion device 10 includes proximal hub 12, distal hub 14, flexible wire connector 16, knob 18, proximal support frame 20 and proximal sheet 22 (which form proximal occluding body 26), distal support frame 28 and distal sheet 30 (which form distal occluding body 32), and atraumatic tips 34. Also, shown are septal wall S, septal defect D, catheter 36, and delivery forceps 38.

Flexible wire connector 16 extends between proximal hub 12 and distal hub 14 to form a center assembly. (Methods of attaching flexible wire connector 16 to proximal and distal hubs 12, 14 will be discussed in detail with reference to FIGS. 6A-6B.) Proximal and distal hubs 12, 14 and flexible wire connector 16 maybe comprised of any suitable material, including Nitinol (a nickel-titanium alloy), titanium or stainless steel. All three components of the center assembly are preferably comprised of the same material to simplify the welding process for assembly purposes. Flexible wire connector 16 is preferably formed to have a diameter of less than about 10 millimeters. In addition, the length of flexible wire connector 16 is preferably less than about 20 millimeters.

Proximal and distal support frames 20, 28 are attached to sheets 22, 30 using sutures to form proximal occluding body 26 and distal occluding body 32 and may be comprised of any number of arms (although only one arm of each of frames 20 and 28 can be seen in FIG. 1). One method of connecting the arms to proximal and distal hubs 12, 14 is to provide proximal and distal hubs 12, 14 with drill holes through which the arms extend. Atraumatic tips 34 are located at the distal end of each arm and serve to minimize damage to the surrounding tissue. Atraumatic tips 34 provide a place for sutures to attach sheets 22, 30 to proximal and distal support frames 20, 28. One method of suturing sheets 22, 30 to proximal and distal support frames 20, 28 is to provide atraumatic tips 34 with drill holes through which sutures pass. In this way, sheets 22, 30 are sewn to support frames 20, 28 at atraumatic tips 34. Proximal support frame 20 is connected to proximal hub 12. Distal support frame 28 is connected to distal hub 14.

More specifically, occlusion device 10 is constructed so that proximal and distal support frames 20, 28 are easily collapsible about proximal and distal hubs 12, 14. Due to this construction, occlusion device 10 can be folded so that proximal and distal support frames 20, 28 are folded in an axial direction. Proximal and distal sheets 22, 30, which are attached to proximal and distal support frames 20, 28, are flexible, and can likewise collapse as proximal and distal support frames 20, 28 are folded. In addition, proximal hub 12 further comprises knob 18, which allows for occlusion device 10 to be grasped by forceps 38 as it is inserted into the body through catheter 36.

Once occlusion device 10 is deployed, support frames 20, 28 must serve to hold proximal and distal sheets 22, 30 in place to seal defect D. To ensure there is sufficient tension to hold sheets 22, 30 in place, support frames 20, 28 are made of a suitable material capable of shape memory, such as Nitinol. Nitinol is preferably used because it is commercially available, very elastic, non-corrosive, and has a fatigue life greater than that of stainless steel. To further ensure that support frames 20, 28 do not suffer from fatigue failures, support frames 20, 28 may be made of stranded wire or cables.

Sheets 22, 30 are comprised of a medical grade polymer in the form of film, foam, gel, or a combination thereof. One suitable material is DACRON®. Preferably, a high density polyvinyl alcohol (PVA) foam is used, such as that offered under the trademark IVALON®. To minimize the chance of occlusion device 10 causing a blood clot, foam sheets 22, 30 may be treated with a thrombosis inhibiting material, such as heparin.

The size of sheets 22, 30 may vary to accommodate various sizes of defects. When measured diagonally, the size of sheets 22, 30 may range from about 15 millimeters to about 45 millimeters. In some instances, it may be desirable to form sheets 22, 30 so that they are not both the same size. For instance, one sheet and its associated fixation device can be made smaller (25 millimeters) than the corresponding sheet and its associated fixation device (30 millimeters). This is particularly useful in situations where occlusion device 10 is to be placed at a location in the heart which is close to other nearby cardiac structures. Making sheets 22, 30 different sizes may assist in providing optimal occlusion of a defect, without affecting other structures of the heart which may be nearby.

FIG. 1A illustrates occlusion device 10 being inserted into septal defect D, which is one example of a cardiac defect that may be occluded using occlusion device 10. Occlusion device 10 is being inserted into septal defect D from catheter 36. Occlusion device 10 is held by delivery forceps 38. To insert occlusion device 10, catheter 36 is positioned proximate septal defect D. Next, delivery forceps 38 is used to push occlusion device 10 through catheter 36 so that distal occluding body 32 unfolds in the left atrium. Although distal occluding body 32 has been deployed, proximal occluding body 26 is still folded in catheter 36.

The placement of catheter 36, or other means that guides occlusion device 10 to septal defect D, determines the location of and angle at which occlusion device 10 is deployed. Once catheter 36 is properly positioned at septal defect D, delivery forceps 38 is used to push occlusion device 10 through septal defect D. Distal occluding body 32 of occlusion device 10 is then allowed to expand against septal wall S surrounding septal defect D.

Wire connector 16 is flexible but remains inside catheter 36 and is therefore immobilized. If wire connector 16 of occlusion device 10 is not flexible (or flexible but immobilized), the center assembly must enter septal defect D following the same angle of insertion as catheter 36 or other delivery device. As a result, the insertion angle is limited by the catheter's angle of insertion.

Often, due to limited space, catheter 36 enters the heart at an angle that is not perpendicular to the defective wall. In this situation, occlusion device 10 cannot enter septal defect D properly because the line of the center assembly must follow the same line as catheter 36. Occlusion device 10 must be forced into septal defect D at an angle, which may cause the tissue surrounding septal defect D to become distorted. If the surrounding cardiac tissue is distorted by catheter 36, it is difficult to determine whether occlusion device 10 will be properly seated once catheter 36 is removed and the tissue returns to its normal state. If occlusion device 10 is not seated properly, blood will continue to flow through septal defect 32 and occlusion device 10 may have to be retrieved and re-deployed. Both doctors and patients prefer to avoid retrieval and re-deployment because it causes additional expense and longer procedure time.

FIG. 1B shows occlusion device 10 with flexible wire connector 16 being inserted into defect D. In FIG. 1B, occlusion device 10 has been further advanced through catheter 36 to expose flexible wire connector 16.

Because wire connector 16 is flexible, the insertion angle of occlusion device 10 is not restricted to that of catheter 36. Occlusion device 10 can be easily inserted, because once flexible wire connector 16 is outside catheter 36, the angle of insertion can be changed by allowing flexible wire connector 16 to move. This variable insertion angle allows occlusion device 10 to enter defect D at an optimum angle, minimizing distortion of surrounding cardiac tissue. If the tissue is not distorted when occlusion device 10 is deployed, the seating of occlusion device 10 should not change drastically once catheter 36 is removed. Because occlusion device 10 can be properly seated at the first insertion, the number of cases that require retrieval and redeployment should decrease.

Figure 1C:
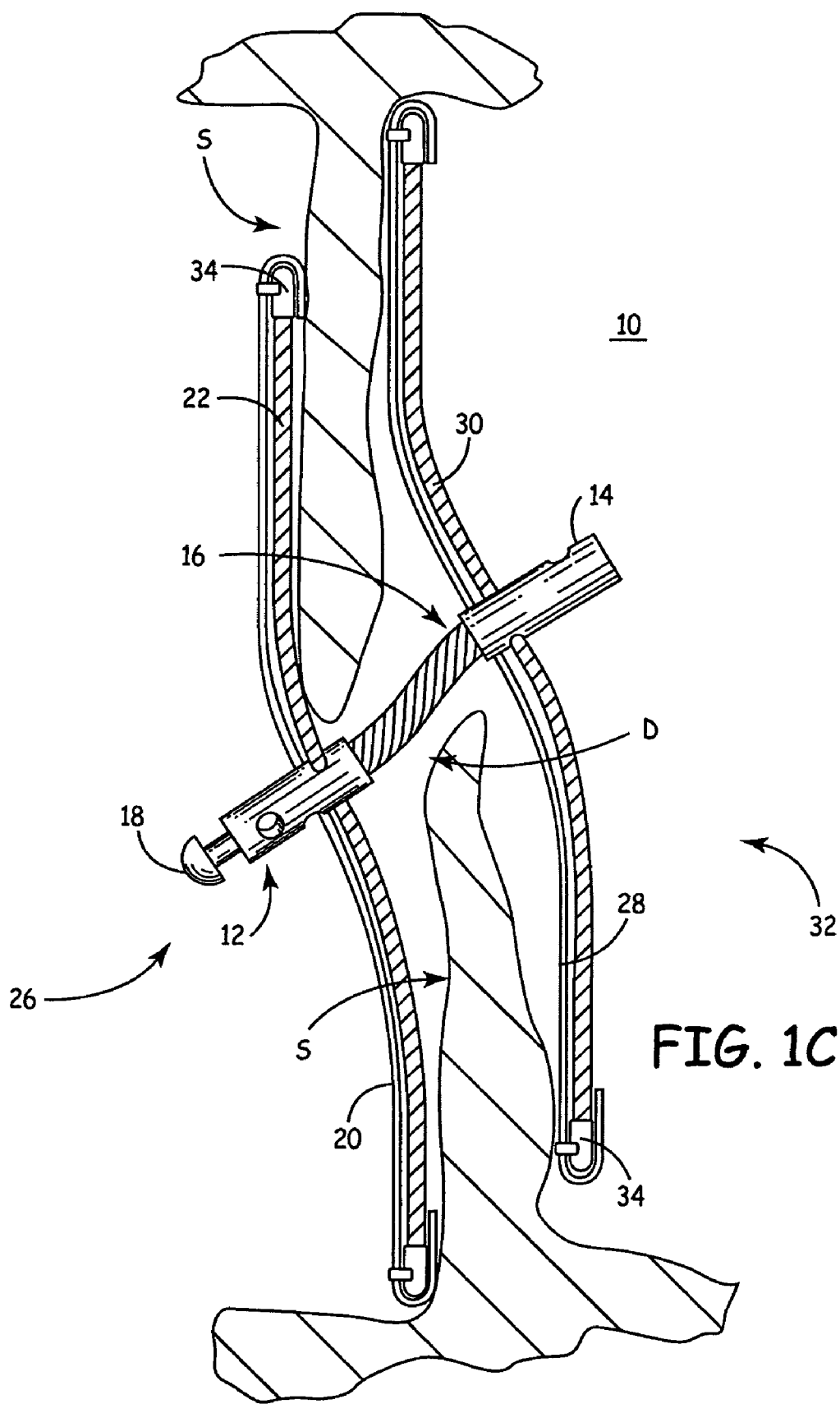
FIG. 1C is a diagram demonstrating the conformation capabilities of the occlusion device of FIGS. 1A-1B.

FIG. 1C shows occlusion device 10, which is fully deployed and is occluding defect D. Shown is occlusion device 10, which includes proximal hub 12, distal hub 14, flexible wire connector 16, knob 18, proximal support frame 20 and proximal sheet 22 (which form proximal occluding body 26), distal support frame 28 and distal sheet 30 (which form distal occluding body 32), and atraumatic tips 34. Also, shown are septal wall S, septal defect D, catheter 36, and delivery forceps 38.

By forming at least a portion of the center assembly to include flexible connector 16, the seating ability of occlusion device 10 is improved without sacrificing any strength (i.e. ability to press against a septal wall) needed to occlude septal defect D or functionality (i.e. ability to move through a catheter, to twist or turn during deployment, to place against a septal wall) needed to properly deploy occlusion device 10.

Flexible wire connector 16 has no negative effect on the ability to move occlusion device 10 through catheter 36. This is because the length of flexible wire connector 16 is preferably less than about 20 millimeters and also because the radial movement of the flexible wire connector is limited to the small diameter of catheter 36. Additional rigidity is created in embodiments having multiple stranded wires (such as the embodiment shown in FIG. 1C) because when flexible wire connector 16 experiences pushing or pulling forces each wire exerts a force on an adjacent wire. As such, flexible wire connector 16 is sufficiently rigid when necessary, such as when proximal and distal hubs 12, 14 are pushed toward one another when occlusion device 10 is moved through catheter 36.

At the same time, flexible wire connector 16 is capable of flexure. When flexible wire connector 16 is not being pushed or pulled or is not experiencing resistance, flexible wire connector 16 does not contact an inner surface of catheter 36 and is more flexible. This flexibility of wire connector 16 allows for occlusion device 10 to be moved easily through sharp turns in a catheter, and allows for occlusion device 10 to be placed so that one side of occlusion device 10 is easily flexible relative to the other side.

Further, once deployed, flexible wire connector 16 is strong enough to hold proximal and distal occluding bodies 26, 32 of occlusion device 10 in place. Thus, flexible wire connector 16 provides the functionality required to deploy occlusion device 10, while offering the benefits of a fully flexible center connector.

In FIG. 1C, distal occluding body 32 has been properly positioned, proximal occluding body 26 has been deployed and occlusion device 10 has been released. FIG. 1C also demonstrates the ability of occlusion device 10 with flexible wire connector 16 to conform to an irregularly shaped septal defect D.

Another important advantage of the present invention is that flexible wire connector 16 allows distal and proximal occluding bodies 26, 32 to conform more readily to the contours of a heart after it is deployed, providing a custom fit to a variety of defects. Often, when implanted, occlusion device 10 is located in an irregularly shaped defect. Having flexible wire connector 16 allows occlusion device 10 to conform to a broader spectrum of defects.

For instance, as viewed in FIG. 1C, septal wall S on the bottom of septal defect D may be only a few millimeters thick, but septal wall S on the top of septal defect D may be much thicker. In such cases, one side of occlusion device 10 may be bent open further than the other side. The side that is more distorted carries a high static load which increases pressure on the surrounding tissue and also increases the possibility of breakage. Because wire connector 16 is flexible, it can bend such that proximal and distal support frames 20, 28 need not be the only the only parts which adjust to fit septal defect D. The ability to conform to a variety of heart contours results in better seating, reduces tension (increasing fatigue life), and decreases the likelihood of damage to tissue resulting from breakage and from pressure exerted on surrounding tissue.

Another feature of occlusion device 10 is that it is fully retrievable. To allow occlusion device 10 to be retrievable, as well as ensure that occlusion device 10 fits into a small diameter catheter, it is important to ensure that the arms of support frames 20, 28 are not of a length that results in atraumatic tips 34 clustering at the same location. If atraumatic tips 34 all cluster at the same location when occlusion device 10 is inside catheter 36, occlusion device 10 will become too bulky to allow it to be easily moved through catheter 36.

Figure 2:
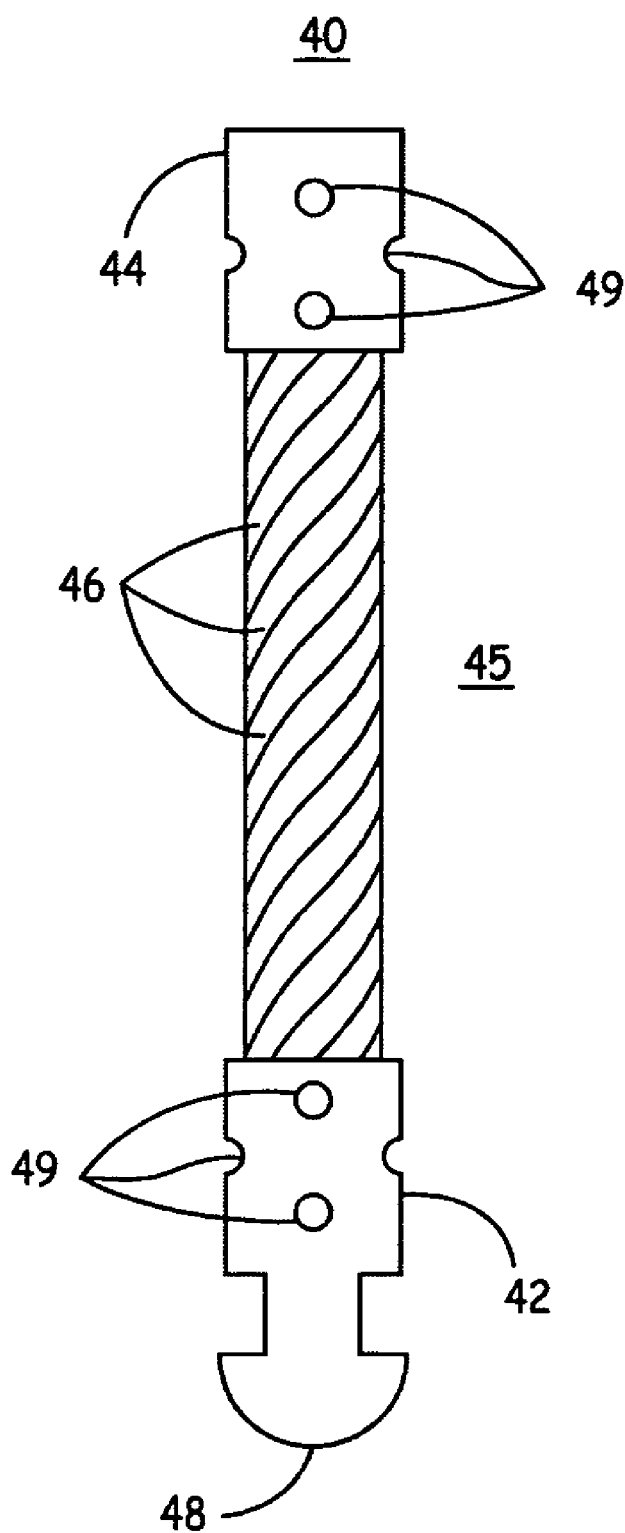
FIG. 2 is a first embodiment of a center assembly for use in an occlusion device where the flexible wire connector is comprised of a multi-wire cable.

FIG. 2 is a first embodiment of center assembly 40 for use in an occlusion device. Center assembly 40 includes proximal hub 42, distal hub 44 and flexible wire connector 45, which comprises wires 46. Also shown is grasping knob 48 and holes 49, which provide a location for attaching the occluding bodies, such as the wire support frames (shown in FIG. 1) to proximal and distal hubs 42, 44.

Flexible wire connector 45 extends between proximal hub 42 and distal hub 44 to form center assembly 40. (Methods of attaching flexible wire connector 45 to proximal and distal hubs 42, 44 will be discussed in detail with reference to FIGS. 6A-6B.) Proximal and distal hubs 42, 44 and flexible wire connector 45 may be comprised of any suitable material, including Nitinol, titanium or stainless steel. All three components of the center assembly can be comprised of the same material to simplify the welding process for assembly purposes. Flexible wire connector 45 is preferably formed to have a diameter of less than about 10 millimeters. In addition, the length of flexible wire connector 45 is preferably less than about 20 millimeters.

Flexible wire connector 45 comprises wires 46, which are cylindrically stranded to form a multi-wire cable. Wires 46 have a diameter of less than about 0.005 inches. Although flexible wire connector 45 may comprise any number of wires, a 1×19 (i.e. one-by-nineteen) configuration provides both the strength and flexibility needed to properly occlude a defect. A 1×19 configuration is formed by wrapping six wires around an individual component wire. Twelve additional wires are then stranded around the 1×7 stranded core to form a multi-wire cable having an overall pitch of about 30 degrees to about 60 degrees.

When flexible wire connector is formed of Nitinol it may be subjected to a precise pre-shaping to give it a "shape-memory." This shape memory helps to hold the strands together, prevent unraveling, and can be used to add pre-tension to wires 46, so that wires 46 can return to their shape even after the strong deformation that occurs when an occlusion device is passed through a catheter. Resulting flexible wire connector 45 is extremely flexible and also has an improved resistance to fatigue (i.e. cracks and breaks resulting from the extreme environment of a heart).

While flexible wire connector 45 is described as a multi-wire cable, it may also comprise a hollow multi-wire tube. One method of forming a multi-wire tube requires removal of the solid 1×7 stranded core from the 1×19 configuration described above. Once the 1×7 stranded core is pulled out of the multi-wire cable, a 1×12 stranded tube is created. Resulting wire connector 45 is more flexible than when comprising a multi-wire cable. In addition, when flexible wire connector 45 comprises a multi-wire cable, flexible wire connector 45 may be connected to proximal and distal hubs 42, 44 as described in FIG. 6B, as well as described in FIG. 6A.

A multi-wire tube formed of cylindrically stranded stainless steel wires is made commercially available by Asahi, Intecc., Ltd. The Asahi tube product may also comprise flexible wire connector 45 and functions similarly to the multi-wire tube described above.

Figure 3:
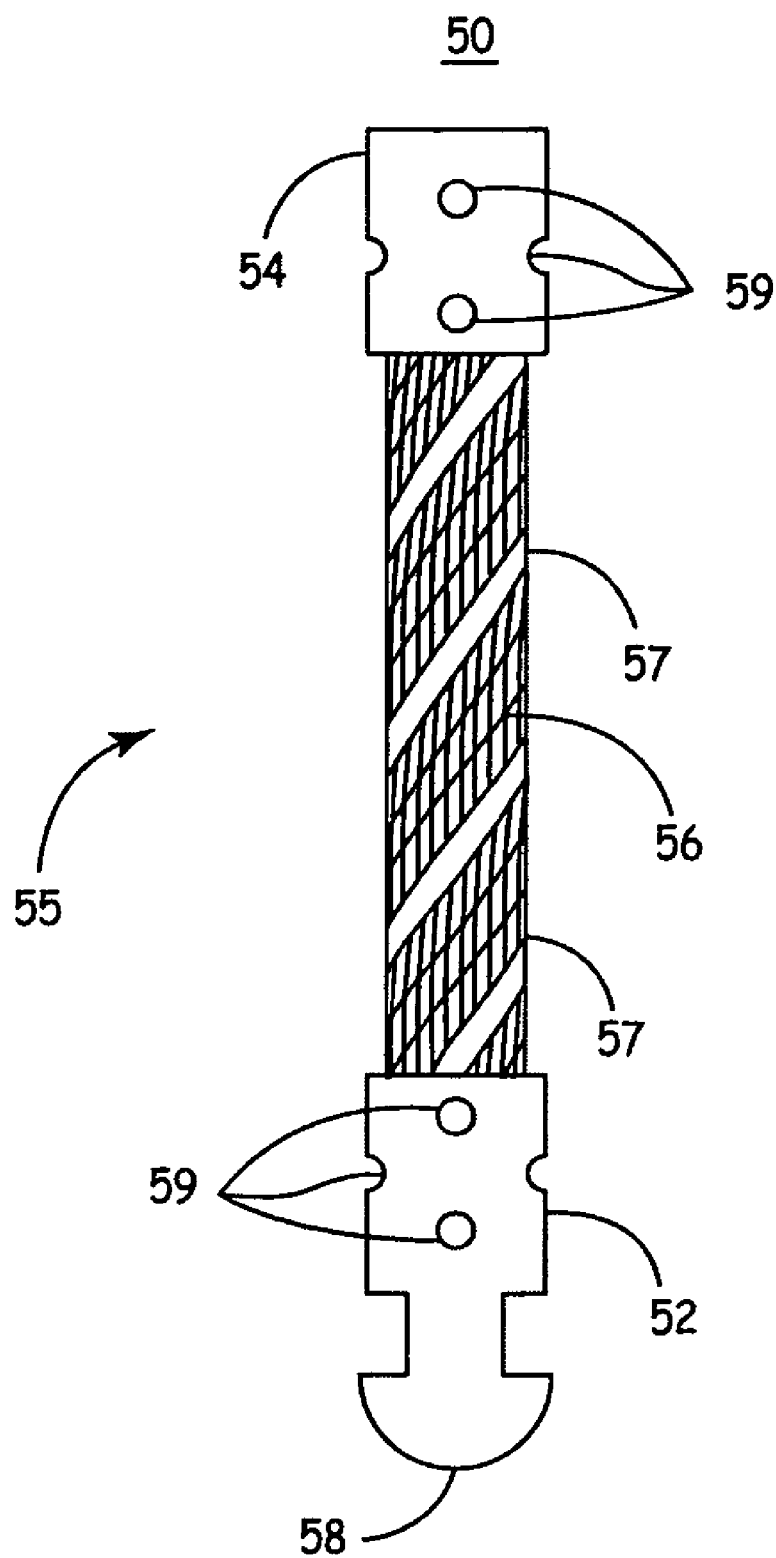
FIG. 3 is a second embodiment of a center assembly for use in an occlusion device where the flexible wire connector is comprised of a multi-wire tube having a wire removed.

FIG. 3 is a second embodiment of center assembly 50 for use in an occlusion device. Center assembly 50 includes proximal hub 52, distal hub 54 and flexible wire connector 55, which comprises wires 56. Also shown is wire removal space 57, grasping knob 58 and holes 59, which provide a location for attaching the occluding bodies, such as the wire support frames (shown in FIG. 1) to proximal and distal hubs 52, 54.

Flexible wire connector 55 extends between proximal hub 52 and distal hub 54 to form center assembly 50. (Methods of attaching flexible wire connector 55 to proximal and distal hubs 52, 54 will be discussed in detail with reference to FIGS. 6A-6B.) Proximal and distal hubs 52, 54 and flexible wire connector 55 may be comprised of any suitable material, including Nitinol, titanium or stainless steel. All three components of the center assembly can be comprised of the same material to simplify the welding process for assembly purposes. Flexible wire connector 55 is preferably formed to have a diameter of less than about 10 millimeters. In addition, the length of flexible wire connector 55 is preferably less than about 20 millimeters.

In the embodiment shown in FIG. 3, one wire out of wires 56, which comprise a multi-wire tube has a segment removed to leave space 57 between remaining wires 56. Removal of the wire may be accomplished by laser cutting or some other means and results in increased flexibility of wire connector 55. Although the ends of flexible wire connector 55 cannot be seen in FIG. 3 since center assembly 50 is assembled, portions of the wire a both ends of the removed segment are left in place. This remaining "collar" connects the end portions of remaining wires 56 to hold wires 56 in place and prevents them from unraveling. Likewise, segments of additional wires 56 may be removed depending upon the desired amount of flexibility. Resulting wire connector is extremely flexible (depending upon the number of wire segments which are removed) and retains sufficient strength to properly occlude a defect.

Figure 4:
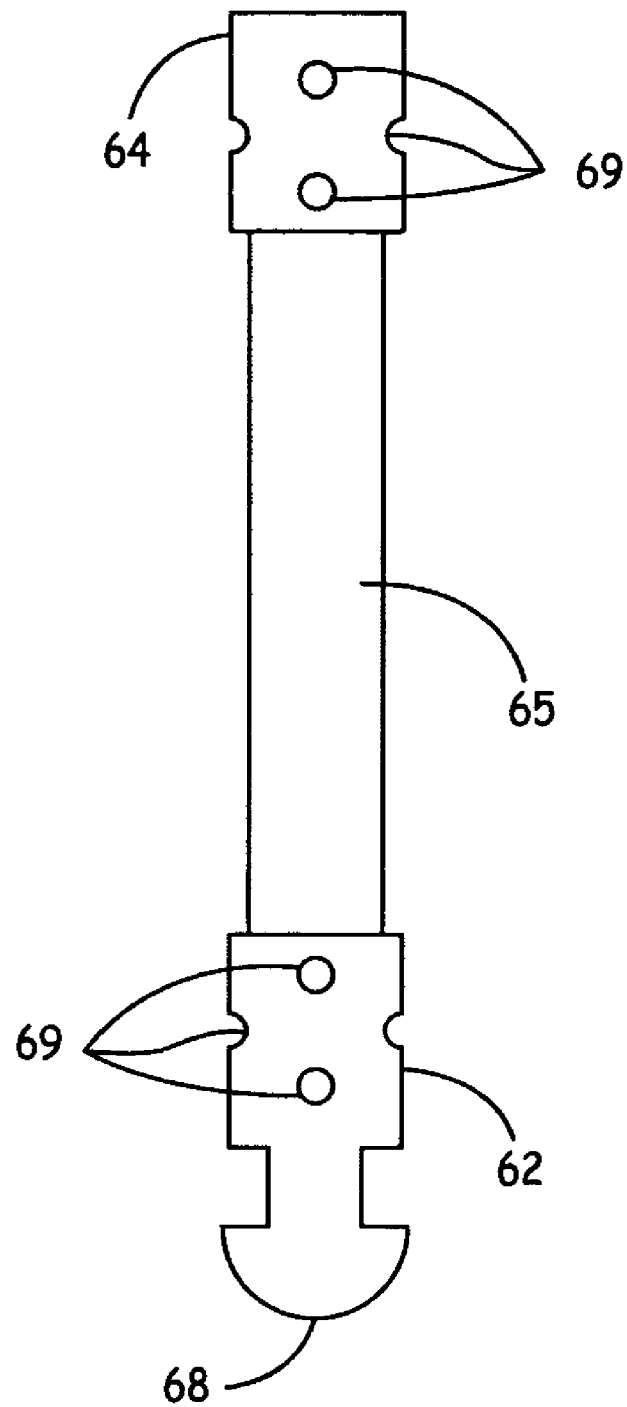
FIG. 4 is a third embodiment of a center assembly for use in an occlusion device where the flexible wire connector is comprised of a single wire.

FIG. 4 is a third embodiment of center assembly 60 for use in an occlusion device. Center assembly 60 includes proximal hub 62, distal hub 64 and flexible wire connector 65. Also shown is grasping knob 68 and holes 69, which provide a location for attaching the occluding bodies, such as the wire support frames (shown in FIG. 1) to proximal and distal hubs 62, 64.

In the embodiment shown in FIG. 4, wire connector 65 comprises a single flexible wire. Flexible wire connector 65 extends between proximal hub 62 and distal hub 64 to form center assembly 60. (Methods of attaching flexible wire connector 65 to proximal and distal hubs 62, 64 will be discussed in detail with reference to FIG. 6A.) Proximal and distal hubs 62, 64 and flexible wire connector 65 may be comprised of any suitable material, including Nitinol, titanium or stainless steel. All three components of the center assembly can be comprised of the same material to simplify the welding process for assembly purposes. Flexible wire connector 65 is preferably formed to have a diameter of less than about 10 millimeters. In addition, the length of flexible wire connector 65 is preferably less than about 20 millimeters.

Figure 5:
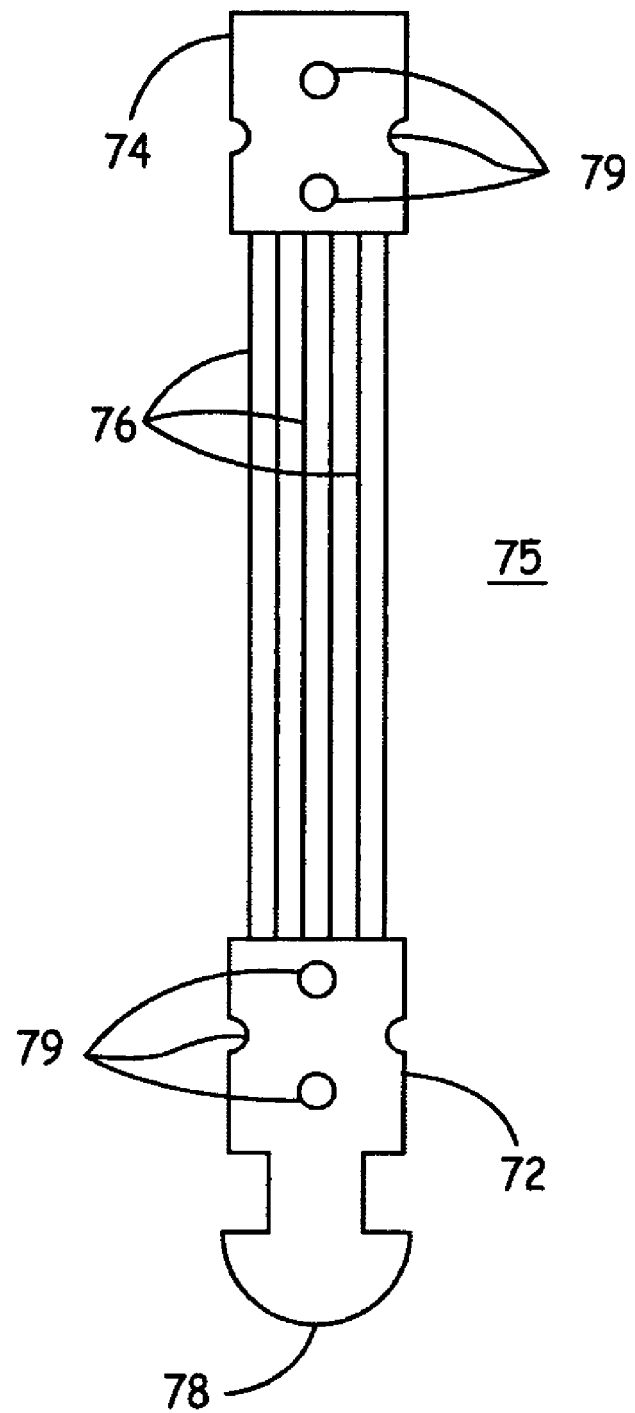
FIG. 5 is a fourth embodiment of a center assembly for use in an occlusion device where the flexible wire connector is comprised of four wires.

FIG. 5 is a fourth embodiment of center assembly 70 for use in an occlusion device. Center assembly 70 includes proximal hub 72, distal hub 74, flexible wire connector 75 and wires 76. Also shown is grasping knob 78 and holes 79, which provide a location for attaching the occluding bodies, such as the wire support frames (shown in FIG. 1) to proximal and distal hubs 72, 74.

Flexible wire connector 75 extends between proximal hub 72 and distal hub 74 to form center assembly 70. (Methods of attaching flexible wire connector 75 to proximal and distal hubs 72, 74 will be discussed in detail with reference to FIGS. 6A-6B.) Proximal and distal hubs 72, 74 and flexible wire connector 75 may be comprised of any suitable material, including Nitinol, titanium or stainless steel. All three components of the center assembly can be comprised of the same material to simplify the welding process for assembly purposes. Flexible wire connector 75 is preferably formed to have a diameter of less than about 10 millimeters. In addition, the length of flexible wire connector 75 is preferably less than about 20 millimeters.

In the embodiment shown in FIG. 5, wire connector 75 comprises wires 76, which are generally parallel and extend in an axial direction. Wires 76 have preferably have a diameter of less than 1 millimeter and are preferably positioned around a perimeter of proximal and distal hubs 72, 74, so wires 76, in essence, form a wire tube. Although the embodiment shown comprises four wires 76 (the fourth wire cannot be seen from this perspective), flexible wire connector may comprise any number of wires 76. For instance, the flexibility of wire connector 75 may be controlled by increasing or decreasing the number of wires 76. If more flexibility is desired, flexible wire connector may comprise fewer wires 76. Additional wires 76 may be added to decrease the flexibility of wire connector 75. In addition, the diameter of wires 76 may be increased or decreased to adjust the desired flexibility of wire connector 75.

Figure 6A:
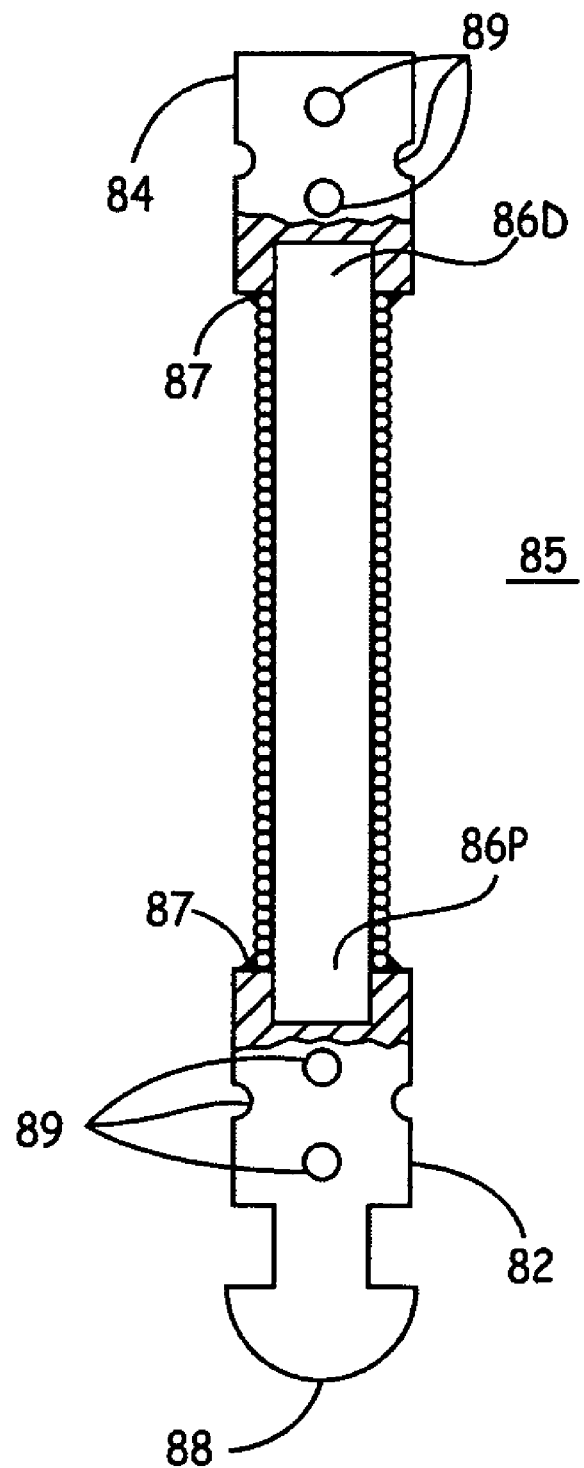
FIG. 6A is a partial cross sectional view of a center assembly in which the flexible wire connector is inserted into a proximal hub and a distal hub.

FIG. 6A is a partial cross sectional view of center assembly 80 demonstrating a first method of connecting a flexible center connector to proximal and distal hubs. Center assembly 80 includes proximal hub 82, distal hub 84 and flexible wire connector 85. Also shown are cavities 86P and 86D, weld joints 87, grasping knob 88 and holes 89.

As shown in FIG. 6A, center assembly is assembled by inserting proximal hub 82 and distal hub 84 flexible wire connector 85. This assembly method may be used to with all of the embodiment described with respect to the present invention. Proximal and distal hubs 82, 84 are provided with drill holes or cavities 86P and 86D, which are sized to correspond to an overall diameter of flexible wire connector 85. Proximal hub 82 is inserted onto a proximal end of flexible wire connector 85. Distal hub 84 is inserted onto a distal end of flexible wires connector 85. Proximal and distal hubs 82, 84 maybe secured to flexible wire connector 85 in any suitable manner. For instance, as shown, proximal and distal hubs 82, 84 are laser welded to flexible wire connector 85 at weld joints 87.

Given the nature of wire connector 85 and the manner in which it is attached to proximal and distal hubs 82, 84, wire connector 85 is extremely flexible, while retaining the ability to transmit torque, push, and pull forces. In addition to being capable of articulation, since flexible wire connector 85 is also capable of transmitting torque, it is possible to rotate an occlusion device including flexible wire connector 85 during deployment. This allows better positioning and seating of the occlusion device.

While it may be necessary to rotate the occlusion device during deployment, it is often not desirable for occluding bodies to be rotatable relative to center assembly 80 or to one another. When the occluding bodies are attached to proximal and distal hubs 82, 84 (as described with respect to FIGS. 1A-1B), the occluding bodies will be prevented from rotating with respect to each other and to center connector 85.

There are several disadvantages to allowing occluder elements to rotate around a center assembly. First, it is possible that the support arms of one support frame will line up with the arms of the other support frame, making it difficult to distinguish one set from the other set when the occlusion device is viewed on a fluoroscope. As a result, it is more of a challenge to determine the exact position of either support frame because when aligned, the two become indistinguishable.

Second, preventing rotation of the occluder elements may improve the overall positioning of the device. For example, when inserting a device that allows freedom of rotation, if upon the insertion of the device, the arms of a support frame are laying in an undesirable position, such as resting against the aorta, simply manipulating the device to reposition the arms may not be possible because the center assembly will spin relative to the occluder element, leaving the arms in the original position.

Third, the preliminary loading of the device may be hindered if rotation of the support frames is not prevented. When the individual occluder elements spin and twirl, loading the occlusion device into a delivery device or catheter may be more difficult and time-consuming.

Figure 6B:
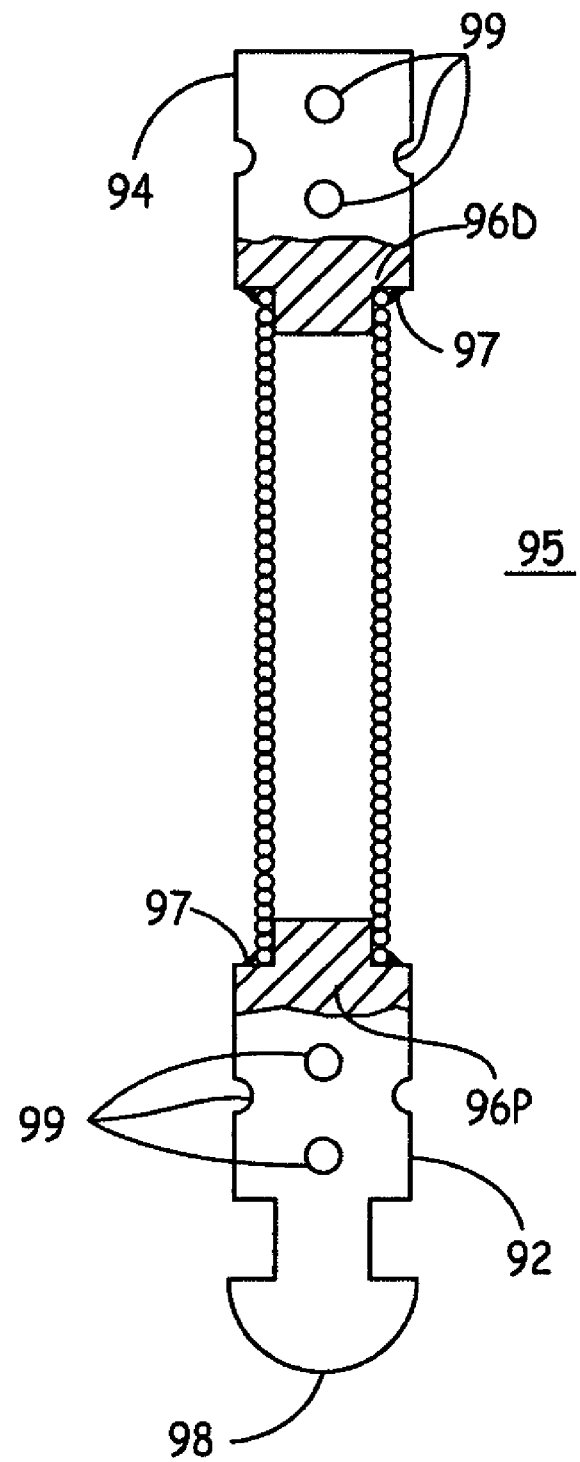
FIG. 6B is a partial cross sectional view of a center assembly in which portions of a proximal hub and a distal hub are inserted into the flexible wire connector.

FIG. 6B is a partial cross sectional view of center assembly 90 demonstrating a second method of connecting a flexible center connector to proximal and distal hubs. Center assembly 90 includes proximal hub 92, distal hub 94 and flexible wire connector 95. Also shown are pegs 96P and 96D, weld joints 97, grasping knob 98 and holes 99.

As shown in FIG. 6B, center assembly 90 is assembled by inserting flexible wire connector 95 onto pegs 96P and 96D of proximal hub 92 and distal hub 94, respectively. This assembly method is preferably used in conjunction with a hollow flexible wire connector, such as those described with respect to FIGS. 2, 3 and 5. However, a solid flexible wire connector, such as flexible wire connector 65, could be provided with drill holes at each end and inserted onto pegs 96P and 96D.

Pegs 96P and 96D are sized to correspond to an inner diameter of flexible wire connector 95. Proximal hub 82 is inserted into a proximal end of flexible wire connector 95. Distal hub 94 is inserted into a distal end of flexible wires connector 95. Proximal and distal hubs 92, 94 may be secured to flexible wire connector 95 in any suitable manner. For instance, as shown, proximal and distal hubs 92, 94 are laser welded to flexible wire connector 95 at weld joints 97. When this assembly method is used, rotation of the occluder bodies is also prevented as described with reference to FIG. 6A.

Figure 7:
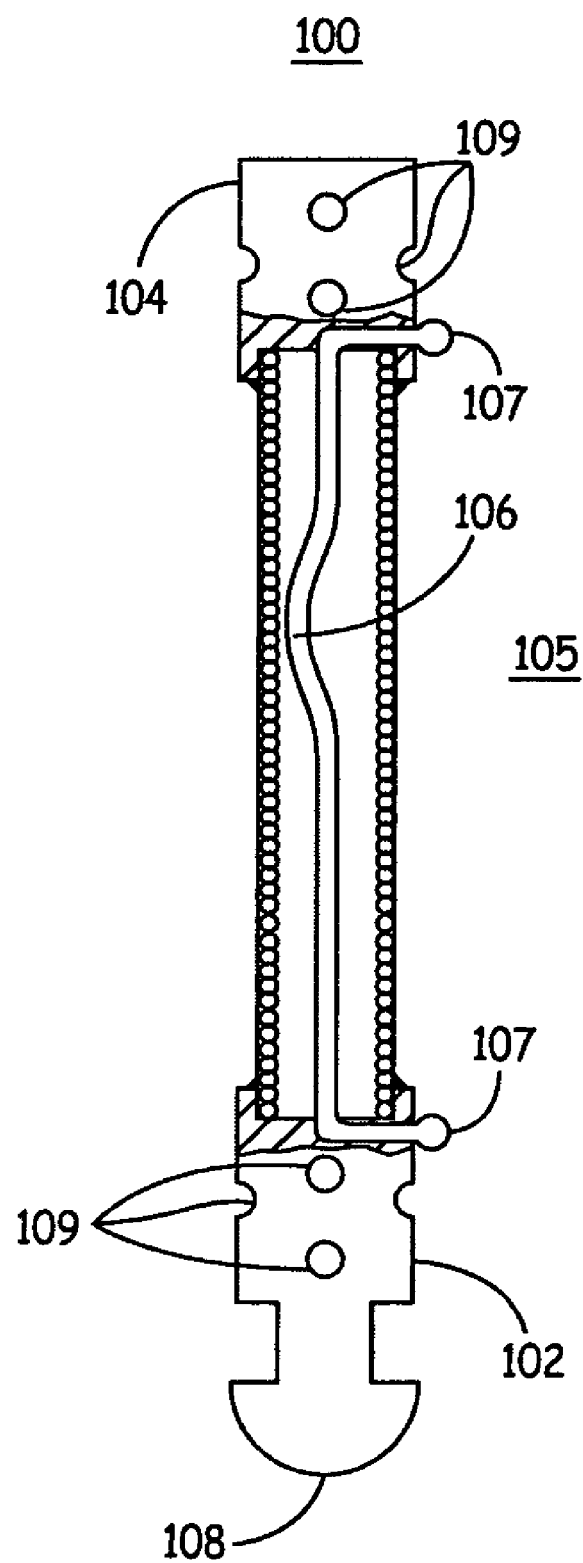
FIG. 7 is a center assembly for use in an occlusion device having a safety tether extending through the flexible wire connector.

FIG. 7 is center assembly 100 for use in an occlusion device having safety tether 106 extending through flexible wire connector 105. Shown is center assembly 100, which includes proximal hub 102, distal hub 104 and flexible wire connector 105. Also shown is safety tether 106, knots 107, grasping knob 108 and holes 109.

Safety tether 106 serves to further ensure the structural integrity of center assembly 100. Safety tether 106 connects proximal hub 102 to distal hub 104 and extends through the middle of flexible wire connector 105. (Therefore, much like the assembly method described with reference to FIG. 6B, safety tether 105 is preferably used with center assemblies having flexible wires connectors which comprise a tube, such as those described with respect to FIGS. 2, 3 and 5.) In this way, safety tether ensures that center assembly 100 remains fully connected while navigating the vasculature of a body and during deployment in a heart.

Safety tether 106 may be comprised of any suitable material, including Nitinol, titanium, stainless steel or polymeric material. In addition, safety tether 106 may be comprised of a single wire or thread or may be comprised of a multi-wire strand, or cable, or a multi-thread fabric braid.

As shown in FIG. 7, safety tether 106 is attached to proximal and distal hubs 102 and 104 by threading it though a cavity in proximal and distal hubs 102 and 104 and securing safety tether 106 to an outside surface of proximal and distal hubs 102 and 104 with knots 107. However, safety tether 106 may be attached to proximal and distal hubs 102 and 104 with any suitable method. For instance, a crimp ring could also be used to attached safety tether 106 to proximal and distal hubs 102 and 104.

Although the present invention has been described with reference to preferred embodiments, workers skilled in the art will recognize that changes may be made in form and detail without departing from the spirit and scope of the invention.

The invention claimed is:

1. An occlusion device comprising:
   a first occluding body including a first collapsible support frame;
   a second occluding body including a second collapsible support frame;
   a center assembly comprising a proximal hub attached to the first occluding body such that the first collapsible support frame extends through the proximal hub, a distal hub attached to the second occluding body such that the second collapsible support frame extends through the distal hub, and a flexible wire connector comprising a hollow multi-wire tube having a proximal end attached to the proximal hub and having a distal end attached to the distal hub; and
   a safety tether having a proximal end attached to the proximal hub, a distal end attached to the distal hub, and central portion extending through a middle of the hollow multi-wire tube.

2. The occlusion device of claim 1 wherein an overall diameter of the flexible wire connector is less than about 10 millimeters and the length of the flexible wire connector is less than about 20 millimeters.

3. The occlusion device of claim 1 wherein the safety tether comprises a wire.

4. The occlusion device of claim 1 wherein the safety tether comprises a braided fabric.

5. The occlusion device of claim 1 wherein the flexible wire connector comprises a plurality of generally parallel wires extending between the proximal hub and the distal hub.

6. The occlusion device of claim 1 wherein the hollow multi-wire tube comprises a multi-wire cable formed from cylindrically stranded wires, the multi-wire cable having a pitch of about 30 degrees to about 60 degrees.

7. The occlusion device of claim 1 wherein at least one wire has been removed from the flexible wire connector.

8. An occlusion device comprising:
   a first collapsible support frame;
   a second collapsible support frame;
   a proximal hub connected to the first collapsible support frame, the first collapsible support frame extending through the proximal hub;
   a distal hub connected to the second collapsible support frame, the second collapsible support frame extending through the distal hub;
   a wire connector comprising a hollow multi-wire tube providing a flexible connection between the proximal hub and the distal hub, the hollow multi-wire tube having a proximal end attached to the proximal hub and a distal end attached to the distal hub;
   at least one safety tether having a proximal end attached to the proximal hub, a distal end attached to the distal hub, and a center portion extending through a middle of the hollow multi-wire tube; and
   a first sheet attached to the first collapsible support frame.

9. The occlusion device of claim 8 and further comprising a second sheet attached to the second collapsible support frame.

10. The occlusion device of claim 8 wherein each of the first and second collapsible support frames includes a plurality of arms.

11. The occlusion device of claim 10 wherein the first collapsible support frame is oriented relative to the second collapsible support frame to offset the arms of the first collapsible support frame from the arms of the second collapsible support frame.

12. The occlusion device of claim 8 wherein an overall diameter of the wire connector is less than about 10 millimeters and the length of the wire connector is less than about 20 millimeters.

13. The occlusion device of claim 8 wherein the wire connector comprises a plurality of generally parallel flexible wires extending between the proximal hub and the distal hub.

14. The occlusion device of claim 8 wherein the hollow multi-wire tube comprises a flexible multi-wire cable formed from cylindrically stranded wires, the flexible multi-wire cable having a pitch of about 30 degrees to about 60 degrees.

15. The occlusion device of claim 8 wherein at least one wire has been removed from the wire connector.

* * * * *

UNITED STATES PATENT AND TRADEMARK OFFICE
CERTIFICATE OF CORRECTION

| | |
|---|---|
| PATENT NO. | : 7,927,351 B2 |
| APPLICATION NO. | : 11/455426 |
| DATED | : April 19, 2011 |
| INVENTOR(S) | : Michael P. Corcoran and Joseph A. Marino |

It is certified that error appears in the above-identified patent and that said Letters Patent is hereby corrected as shown below:

Col. 2, Line 56
  Delete "maybe"
  Insert --may be--

Col. 9, Line 62
  Delete "attached"
  Insert --attach--

Signed and Sealed this
First Day of May, 2012

David J. Kappos
*Director of the United States Patent and Trademark Office*